United States Patent
Goudberg et al.

(10) Patent No.: US 7,361,259 B2
(45) Date of Patent: Apr. 22, 2008

(54) CAPILLARY ARRAY AND ELECTROPHORESIS APPARATUS, AND METHOD

(75) Inventors: Johan R. P. Goudberg, San Jose, CA (US); Syouzou Kasai, Hitachinaka (JP)

(73) Assignee: Applera Corporation, Foster City, CA (US)

( * ) Notice: Subject to any disclaimer, the term of this patent is extended or adjusted under 35 U.S.C. 154(b) by 349 days.

(21) Appl. No.: 10/440,572

(22) Filed: May 19, 2003

(65) Prior Publication Data

US 2004/0000481 A1    Jan. 1, 2004

(30) Foreign Application Priority Data

May 17, 2002   (JP)   ............... 2002-142294

(51) Int. Cl.
*G01N 27/453* (2006.01)
(52) U.S. Cl. ..................... 204/603; 204/601
(58) Field of Classification Search ........ 204/451–455, 204/601–605
See application file for complete search history.

(56) References Cited

U.S. PATENT DOCUMENTS

| | | | |
|---|---|---|---|
| 4,424,127 A | * | 1/1984 | Roeraade ................. 210/198.2 |
| 5,582,705 A | | 12/1996 | Yeung et al. |
| 5,790,727 A | | 8/1998 | Dhadwal et al. |
| 5,885,430 A | | 3/1999 | Kernan et al. |
| 6,017,434 A | | 1/2000 | Simpson et al. |
| 6,054,032 A | | 4/2000 | Haddad et al. |
| 6,162,341 A | | 12/2000 | Nordman et al. |

(Continued)

FOREIGN PATENT DOCUMENTS

| | | |
|---|---|---|
| EP | 1 006 355 A2 | 6/2000 |
| WO | WO 96/36872 | 11/1996 |

(Continued)

OTHER PUBLICATIONS

ABI Prism® 3100 Genetic Analyzer—User's Manual, Applied Biosystems/Hitachi, pp. 2-24, 2-26, and 8-15 (2001).

(Continued)

*Primary Examiner*—Alex Noguerola
(74) *Attorney, Agent, or Firm*—Kilyk & Bowersox, P.L.L.C.

(57) ABSTRACT

A capillary electrophoresis device including a capillary array, and a method of manufacturing the capillary array, are provided. During the manufacture of the capillary array, a plurality of capillaries are arranged in a substantially parallel arrangement and are fixed with a fixing member, to form a ribbon-shaped member. A detection cell can be arranged on the ribbon shaped member. The capillary array can achieve uniform heat dissipation thereby allowing electrophoretic velocity to be independent of the temperature characteristics of the capillaries. The plurality of capillaries are not attracted or repelled to each other by way electrostatic effects during electrophoresis, and the productivity of the capillary array can be improved.

27 Claims, 16 Drawing Sheets

U.S. PATENT DOCUMENTS

| | | | |
|---|---|---|---|
| 6,461,492 B1 * | 10/2002 | Hayashizaki et al. | 204/603 |
| 6,560,859 B1 * | 5/2003 | Hayashizaki et al. | 29/789 |
| 6,562,214 B1 * | 5/2003 | Amrhein et al. | 204/601 |
| 6,675,446 B2 * | 1/2004 | Buettell | 24/122.6 |
| 6,878,256 B2 * | 4/2005 | Kasai et al. | 204/604 |
| 2001/0040094 A1 | 11/2001 | Inaba et al. | |
| 2002/0003091 A1 | 1/2002 | Kojima et al. | |
| 2002/0023839 A1 * | 2/2002 | Inaba et al. | 204/451 |

FOREIGN PATENT DOCUMENTS

| | | |
|---|---|---|
| WO | WO 01/84134 A1 * | 11/2001 |

OTHER PUBLICATIONS

Lu et al., Optimization of Excitation and Detection Geometry for Multiplexed Capillary Array Electrophoresis of DNA Fragments, *Applied Spectroscopy*, vol. 49, No. 5, pp. 605-609 with cover, (May 1995).

Notification of, and International Search Report, mailed Nov. 10, 2003, for International Application No. PCT/US03/15797.

* cited by examiner

CAPILLARY ARRAY AND ELECTROPHORESIS APPARATUS, AND METHOD

CROSS-REFERENCE TO RELATED APPLICATION

This application claims priority benefit under 35 U.S.C. §119(a) from Japanese Patent Application No. 2002-142294 filed May 17, 2002, which is incorporated in its entirety by reference. The subject matter of the present application was developed under a joint research agreement between Perkin Elmer Corporation, through its PE Applied Biosystems Division, and Hitachi, Ltd., through its Instrument Division. The Perkin Elmer Corporation reorganized and changed its name to PE Corporation in 1999, and further changed its name to Applera Corporation, and changed the name of PE Applied Biosysterns Division to Applied Biosystems in 2002.

FIELD

The present teachings relate to a capillary array electrophoresis device for separating and analyzing samples, such as DNA or proteins.

BACKGROUND OF THE INVENTION

Known capillary electrophoresis devices are disclosed in Japanese Kokai Patent Applications Nos. Hei 11 [1999]-230938, 2000-131278, and 2000-162180.

Japanese Kokai Patent Application No. Hei 11 [1999]-230938 describes the use of a solid member that can hold capillaries. The solid member has notches that are arranged at prescribed spacings from each other, and a capillary can be inserted in each notch and held.

Japanese Kokai Patent Application No. 2000-131278 describes the use of a detection-side holder that can hold capillaries side-by-side along a plane. In the holder, capillaries can be fixed when they are sandwiched between a lower holder plate and an upper rubber plate.

Japanese Kokai Patent Application No. 2000-162180 describes a method for manufacturing a capillary array that includes three steps, steps A-C. In step A, the end portions of the capillaries of the array are aligned, and a filler is coated onto a surface of the end portions. In step B, the coated end portions are bundled, and the bundle is inserted into a thermal shrinking tube. In step C, the thermal shrinking tube is heated and shrunk.

SUMMARY OF THE PRESENT INVENTION

The present teachings disclose a capillary array that can provide improved productivity. The present teachings disclose a capillary electrophoresis device that can achieve uniform electrophoretic velocity of samples through each of the capillaries of the capillary array.

The present teachings provide a method of manufacturing a capillary array including a plurality of capillaries that can be held substantially parallel to each other by way of a fixing member, and can be used in such an arrangement while conducting electrophoresis. As a result, capillaries that have been previously prone to repulsion or attraction due to electrostatic forces can now be handled and controlled more readily.

The present teachings also provide a capillary array including a plurality of capillaries that can be arranged substantially parallel to each other over a predetermined length by way of a fixing member. The electrophoretic velocity of samples are temperature dependent, and by arranging the capillaries in a substantially parallel arrangement, they can be provided with substantially the same temperature characteristics during electrophoresis. As a result, the present teachings allow the electrophoretic velocity of the samples to be less dependent on the temperature characteristics of the capillaries.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description herein.

It is to be understood that both the foregoing general description and the following detailed description are exemplary and explanatory only, and are intended to provide an explanation of various embodiments of the present teachings.

DESCRIPTION OF VARIOUS EMBODIMENTS

APPLICATION EXAMPLE 1

Figure 2:
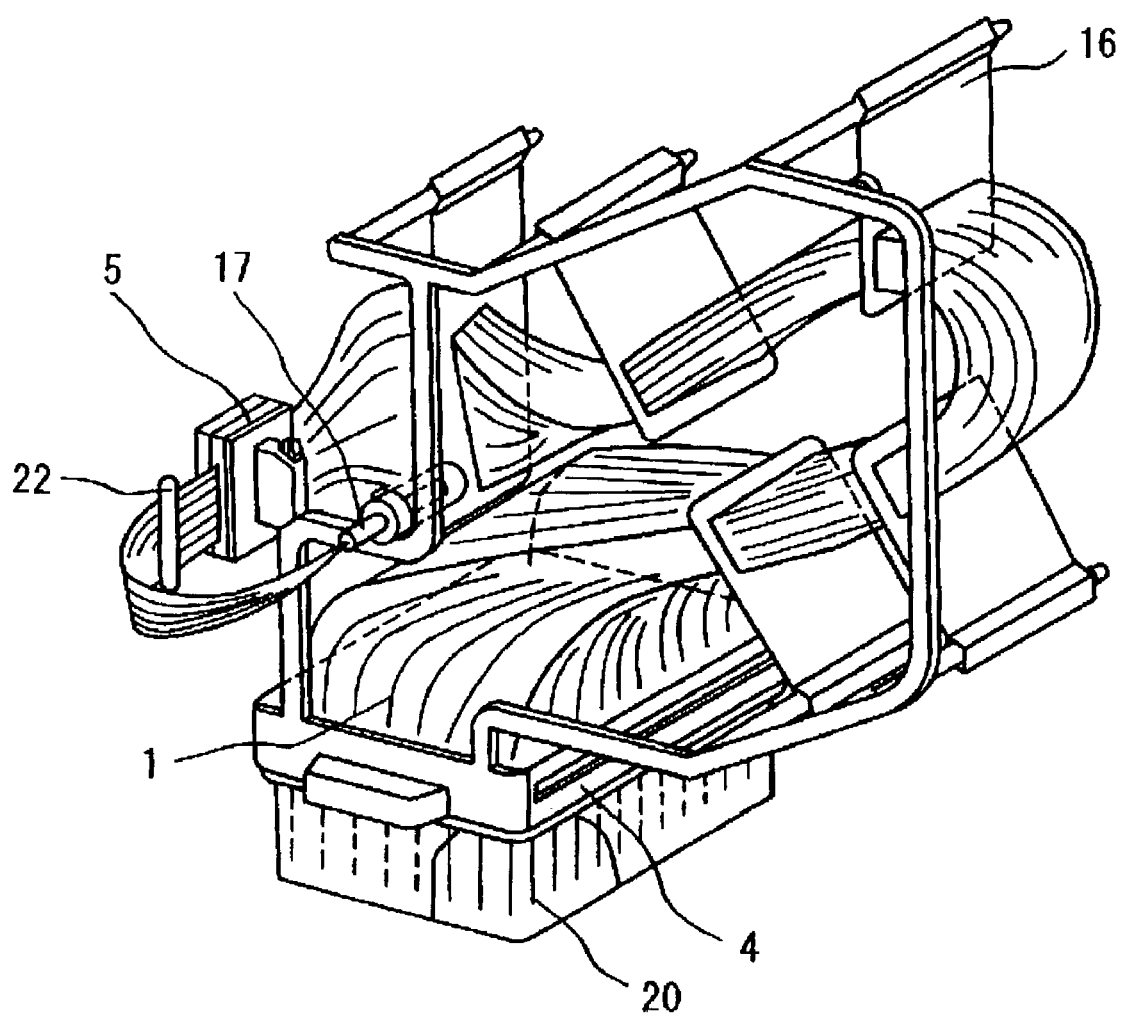
FIG. 2 is a perspective view of a capillary array according to various embodiments.
Figure 3:
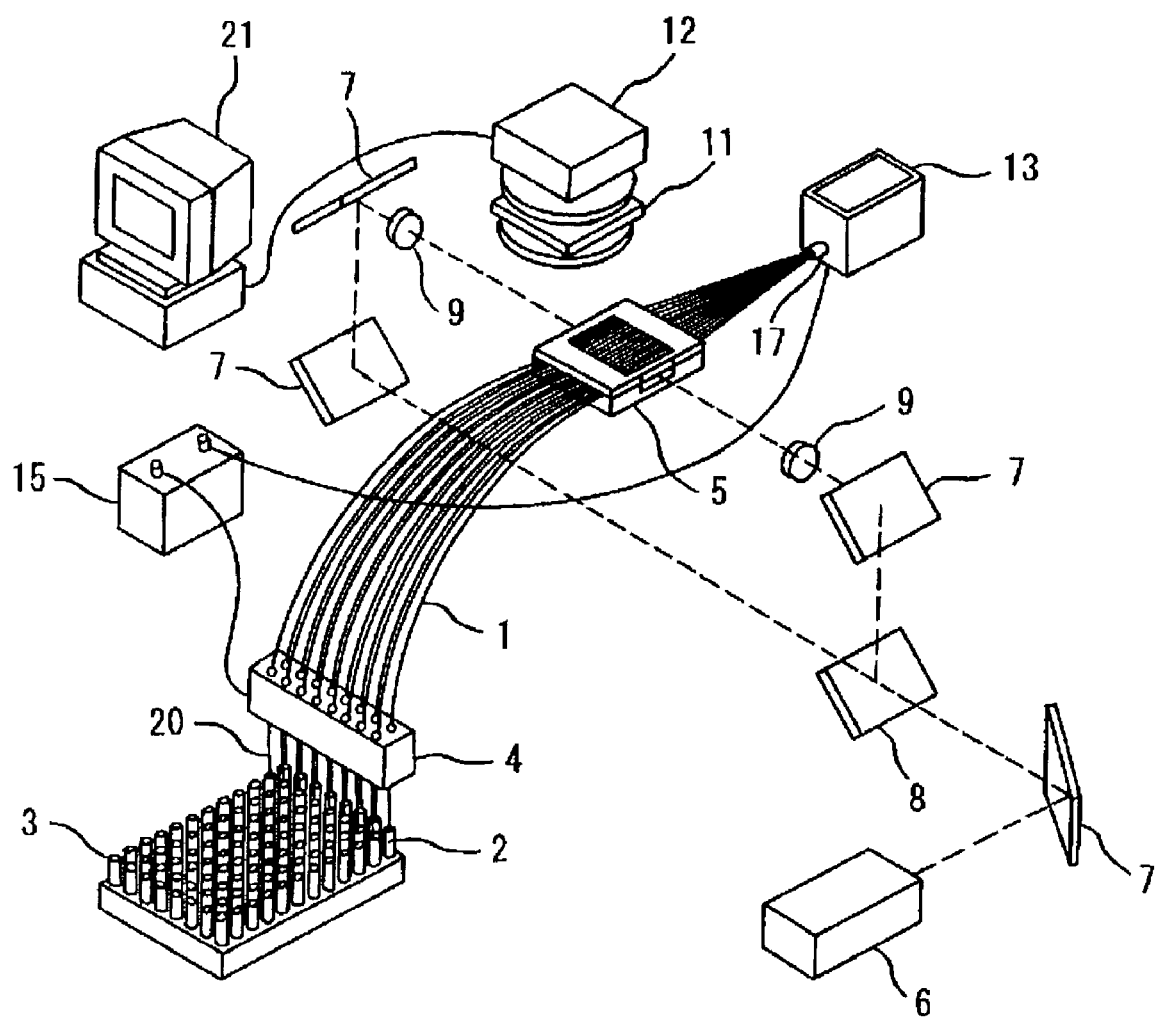
FIG. 3 is a schematic perspective view of a capillary array electrophoresis device according to various embodiments.

FIG. 3 is a schematic diagram of a capillary electrophoresis device according to various embodiments. FIG. 2 is a perspective view of a capillary array according to various embodiments.

According to various embodiments, the capillary electrophoresis device can include a capillary array, a sample tray, a power supply unit, and an optical system. The capillary array can be a replaceable member and can include a plurality of capillaries 1 for conducting electrophoretic separation of a sample under analysis. The capillaries 1 of the array are replaceable, and the use of a capillary array allows easy installation of the capillaries 1 onto a main body of the capillary electrophoresis device. The sample tray 3 (see FIG. 3) can be a container that can hold one or more samples for examination. The power supply unit can be a mechanism that generates an electric field for conducting electrophoretic separation of the sample. The optical system can be a mechanism that can fluorescence a sample and can detect the emitted fluorescence. The structures of the various parts of an electrophoresis device will be explained below.

According to various embodiments, the capillary array can include a plurality of capillaries 1, a load header 4, a capillary head 17, a detection cell 5, and one or more separators 16. The capillary array can be a replaceable member that can be connected to the main body of the electrophoresis device in a quick-connecting and disconnecting manner. After several months of use, or after several hundred cycles of electrophoresis operation, the ability of the capillary array to separate samples can become reduced, and the capillary array can then be disposed.

According to various embodiments, a capillary 1 can be a hollow member that can be capable of electrophoretic separation of samples. The capillaries 1 can be made of a fused-silica pipe, for example, and can have an outer diameter of about 0.15 mm and inner diameter of about 0.05 mm. The outside surface of each capillary 1 can be coated with a resin coating, such as polyimide. The capillaries 1 can include a light-illuminable portion that can be illuminated with light, such as a laser beam. At the light-illuminable portion, the coating is not applied or can be removed. A separation medium that can be injected, together with a buffer liquid, into each capillary 1. During electrophoresis, the separation medium can promote differences in electrophoretic separation. The inlet end of each capillary 1 can be dipped into the sample to be analyzed. For example, into the inlet end of each capillary 1 a sample, such as DNA, can be injected by way of electrophoresis.

According to various embodiments, the load header 4 can hold one end of the capillaries 1. The load header 4 can hold a plurality of hollow electrodes 20 that can be arranged in an array of 8 rows and 12 columns. The hollow electrodes 20 can be made of five stainless steel tubes, for example. Each capillary 1 can be arranged to extend through a hollow electrode 20, and the inlet end of each capillary can protrude slightly from an end portion of the hollow electrode 20. By way of an epoxy-based adhesive, for example, each capillary 1 can be fixed to a respective hollow electrode 20. The load header 4 can support the inlet end portion of each capillary 1 at a position corresponding to a sample container 2 by way of a hollow electrode 20.

According to various embodiments, a detection cell 5 can detect fluorescence that has been emitted from the sample upon illuminating the sample light, to thereby obtain information from the sample. The detection cell 5 can arrange and fix a plurality of capillaries 1, 96 capillaries for example, in an array with a precision of a few microns on a reference base that can operate as a flat optical plane. The capillaries 1 can be arranged substantially parallel in an order by way of the load header 4. During electrophoresis, a laser beam can be directed through the light-illuminable portions of the capillaries 1, such that fluorescence can be emitted from the sample. By detecting the fluorescence with the detection cell 5, it is possible to obtain information from the sample.

According to various embodiments, a capillary head 17 can bundle opposite end portions of the capillaries 1 that are arranged opposite to the load header 4. The capillary head 17 can allow the opposite end portions of the capillaries 1 to be attached in a quick-connecting and disconnecting manner to the buffer liquid container 13 of the main body of the electrophoresis device, in a pressure-proof and a gas-tight manner. A buffer that is held in the buffer liquid container 13 can be filled into the capillaries 1.

According to various embodiments, at least one separator 16 can hold the capillaries 1 at a prescribed spacing from each other. The separator 16 can be a plate-shaped member that can include a plurality of holes in the shape of an array. The holes can be slightly larger than the diameter of the capillaries 1. Each hole can allow one capillary 1 to be inserted through it and can act to hold the plurality of capillaries 1 at a prescribed spacing from each other. As a result, the separator 16 can ensure a uniform temperature distribution between the capillaries 1 during electrophoresis, so as to provide uniform heat dissipation for the capillaries 1.

According to various embodiments, the sample tray 3 can be a container for holding one or more samples. In the sample tray 3, multiple sample containers 2 can be held in an array. Each sample container 2 can contain at least about 10 microliters of sample. For example, each sample can contain a nucleic acid labeled by way of fluorescence labeling for identifying the 4 types of nucleotide base molecules. The nucleic acid can be part of a longer chain of nucleic acids such as a DNA fragment. The inlet end portion of each capillary 1 can be dipped into a sample contained in a sample container 2. By way of electrophoresis, the sample can be fed into the capillary 1.

According to various embodiments, the optical system can direct excitation wavelengths of light onto the detection cell 5 and can detect the light emitted from the sample and the detection cell 5. The optical system can include an excitation wavelength optical system that can include a laser beam for producing excitation light, and a detecting optical system for detecting emission wavelengths that contain information emitted from the sample.

According to various embodiments, the excitation wavelength optical system can include a laser light source 6, a mirror 7, a beam splitter 8, and a light condensing lens 9. A laser beam can be directed from two opposite directions onto the detection cell 5 to fluorescence the samples in the capillaries 1. The laser beam can be focused by way of a lens-type function of the capillaries 1, and it can be passed through all of the capillaries 1. According, to various embodiments, the direction of the laser beam can be switched, and the laser beam can be directed onto the light-illuminable portions of the capillaries 1 in a time-division configuration.

According to various embodiments, the detecting optical system can include a detecting lens system 11 for detecting fluorescence 10 emitted from the sample, and a CCD camera 12. A computer 21 can be a signal processing device that can process information from the fluorescence 10 that is output from the CCD camera 12.

According to various embodiments, the power supply system can include a high-voltage power supply 15, the hollow electrodes 20, and a buffer liquid container 13. A high voltage of about 15 kV can be supplied from the high-voltage power supply 15 along a power feeding path. The power feeding path can include the hollow electrodes 20, the samples in the sample containers 2, the buffer liquid in the capillaries 1, and a liquid buffer in the buffer liquid container 13. The high voltage can be supplied such that a negative potential is applied to the hollow electrodes 20, and a positive potential is applied to the buffer liquid in the buffer liquid container 13. According to various embodiments, the electric field applied along the power feeding path can be directed along a direction from the liquid buffer in buffer liquid container 13 to hollow electrodes 20. According to various embodiments, a negatively charged sample can be moved during electrophoresis from the sample container 2 to the detection cell 5.

Methods of sample analysis using the capillary electrophoresis device according to various embodiments are discussed below.

According to various embodiments, when a high voltage is applied to the power feeding path, the sample contained in the sample container 2 can enter the inlet end portion of the capillary 1. This occurs because the sample, a nucleic acid, for example, can be negatively charged, while the interior of capillary 1 can be positively charged with respect to the sample container 2. After a prescribed amount of the sample enters into capillary 1, the hollow electrode 20 can be removed from the sample container. The hollow electrode 20 can then be dipped into the buffer liquid and electrophoresis can be continued.

According to various embodiments, when samples having different sizes pass through the electrophoresis path formed by the separation medium filled in the capillaries 1, the components of the samples can reach the light-illuminable portion sequentially, with the smaller components reaching the light-illuminable portion earlier. As the sample is illuminated with a laser beam at the light-illuminable portion, fluorescence wavelengths corresponding to characteristics of the sample, such as the 4-types of nucleotide bases that have been labeled, can be emitted. The fluorescence that can be emitted can correspond to the nucleotide bases of adenine, guanine, cytosine, and thymine. By detecting the fluorescence, followed by conducting an analysis by the computer 21, the sample can be analyzed.

The relationship between the temperature of the capillaries 1 and the electrophoresis velocity of the sample, such as nucleic acid, will be disclosed. The relationship between temperature, T, of the capillary 1, and the velocity, V, of electrophoresis of the sample in the capillary 1 can be represented by:

$$V = kT \quad k: \text{proportional constant}$$

To achieve uniform electrophoretic velocity throughout the various capillaries 1, it is desirable to have the same temperature characteristics in all or substantially all of the capillaries 1.

As shown in FIG. 3, the capillaries 1 can include three structural members, and various methods can be adopted to keep the shape of the capillaries 1. The capillaries 1 can be bundled at the capillary head 17, and they can be arranged side-by-side in a parallel relationship to each other on the reference base at the detection cell 5. In the area between the detection cell 5 and the load header 4, the capillaries 1 can be separated individually with a separator 16 (see FIG. 1(*b*), and the capillaries 1 can be held individually by way of hollow electrodes 20 in the vicinity of the load header 4. The capillary head 17 can be connected to the buffer liquid container 13; the load header 4 can be connected to the sample tray 3; and the detection cell 5 can be connected to the optical system. In this state, nonuniformity in temperatures can take place because of heat dissipation from the plurality of capillaries 1. As a result the capillary electrophoresis device can be provided with a temperature control mechanism to achieve highly precise, uniform temperature characteristics for the plurality of capillaries 1.

Figure 5A:
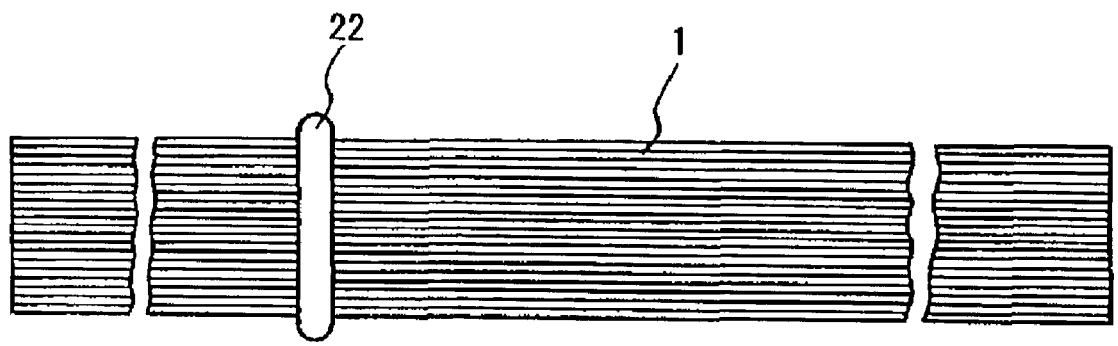
FIG. 5(a) is a schematic diagram of a top view of a ribbon-shaped portion of a capillary array according to various embodiments.
Figure 5B:
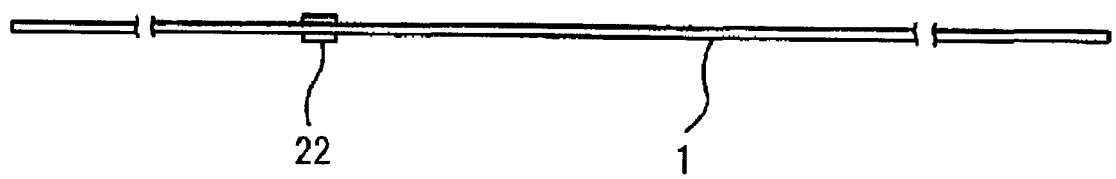
FIG. 5(b) is a schematic diagram of a side view of the ribbon-shaped portion of the capillary array of FIG. 5(a) according to various embodiments.

FIGS. 5(*a*) and 5(*b*) are schematic diagrams of a ribbon-shaped member that can be prepared in the third step, disclosed below. FIGS. 1(*a*) and 1(*b*) are schematic diagrams of the capillary array intermediate body that can be prepared in the ninth step, disclosed below. The manufacturing steps for the capillary array according to various embodiments will be disclosed below.

The manufacturing process can have the following 10 steps:

$1^{st}$ step (capillary cutting step): In this step, a feed capillary wire that can be wound on a drum can be cut to form capillaries having a prescribed length.

$2^{nd}$ step (capillary counting step): In this step, the necessary number of cut capillaries for a unit are counted and assigned, and the capillaries are arranged as a bundle.

$3^{rd}$ step (capillary bundle aligning step): In this step, the bundle of capillaries can be aligned on one end, and the bundle-aligned sheet can be heat-pressed at the fixing member to form the ribbon-shaped member that can facilitate handling of the capillaries.

$4^{th}$ step (capillary head mounting step): In this step, the capillary head can be attached on one end of the capillaries forming the ribbon-shaped member.

$5^{th}$ step (capillary coating-removing step): In this step, the portion of the polyimide coating on the capillaries at the light-illuminable portion can be removed.

$6^{th}$ step (step of aligning and fixing on a reference base): In this step, the ribbon-shaped member can be arranged on a flat reference base with the capillaries arranged in parallel with high precision to form the detection cell.

$7^{th}$ step (separator mounting step): In this step, the capillaries can be fed through the various holes on a separator, and the separator can be mounted.

$8^{th}$ step (load header mounting step): In this step, the capillaries can be fed through the hollow electrodes mounted on the load header, and can be fixed with an adhesive. The load header can then be mounted.

$9^{th}$ step (step of mounting covers on the capillary head and the load header): In this step, covers can be mounted on the capillary head and the load header, respectively, without causing contamination.

$10^{th}$ step (frame mounting step): In this step, after a frame is mounted onto the load header, the separator, the detection cell, and the capillary head can be mounted to the frame.

During the manufacturing process, the following three principles can be observed:

(1) The number of steps in which multiple capillaries are individually handled should be minimized.

(2) The members for mounting the capillaries 1 should be mounted starting from the smallest.

(3) The members for mounting the capillaries 1 should be mounted starting from the lightest.

At least these three principles should be observed to avoid the following problems:

(1) As the polyimide coating of the capillaries 1 is charged with an electrostatic charge, the capillaries 1 can repel each other. As a result, it can be difficult to align a plurality of capillaries 1 in a row.

(2) The manual operation of individually aligning the capillaries 1 with high precision onto the reference base of the detection cell 5 can be difficult and can require high skill and patience. It can be extremely difficult to align 20 or more capillaries.

(3) It can be difficult to individually arrange a plurality of capillaries 1 with high precision in a row and with an equal spacing between them on a reference base.

(4) When a plurality of capillaries are handled in a dispersed state during operation, the capillaries can fall off from the bundle, and the number of capillaries in the bundle can be reduced.

(5) The plurality of capillaries having lengths of at least about 10 mm and diameters of about 0.15 mm cannot hold their own weight, and they can be prone to bending. As a result, the ability to handle the capillary array during manufacturing can be poor. The capillaries 1 can have a low strength, and there is a high possibility of damage.

In the following, a detailed explanation will be made of the $3^{rd}$ through $6^{th}$ manufacturing steps:

$3^{rd}$ step (capillary bundle aligning step): In this step, a ribbon-shaped member having a width of about 10 mm to about 20 mm can be formed utilizing, for example, 96 capillaries 1, that have been counted in the $2^{nd}$ step.

In the wintertime, when the humidity around general insulators becomes 30-50% or lower, electrostatic charge can occur as a result of friction. The voltage of the electrostatic charge on the insulators can be in the range of about several hundred to about several thousand volts. When charging at such voltage takes place, portions possessing the same sign can repel each other, and portions of the opposite signs can attract each other. The polyimide coating on the capillaries 1 can be an insulator, and it can be negatively charged in a cutting operation, for example. As a result, repulsion between the capillaries 1 can take place relatively easily, and it may be difficult to handle multiple capillaries at the same time. However, when a ribbon-shaped member is formed, even when electrostatic charging takes place on the capillaries 1 due to friction with other members, the capillaries 1 will not move apart due to repulsion. In the capillary coating removing step ($5^{th}$ step) and in the step of aligning and fixing on the reference base ($6^{th}$ step), as well as other subsequent steps, operation can be carried out quickly and reliably. In addition, the 96 capillaries 1 can be fixed, and the rigidity of the capillaries 1 can be increased by forming the ribbon-shaped member.

Figure 13:
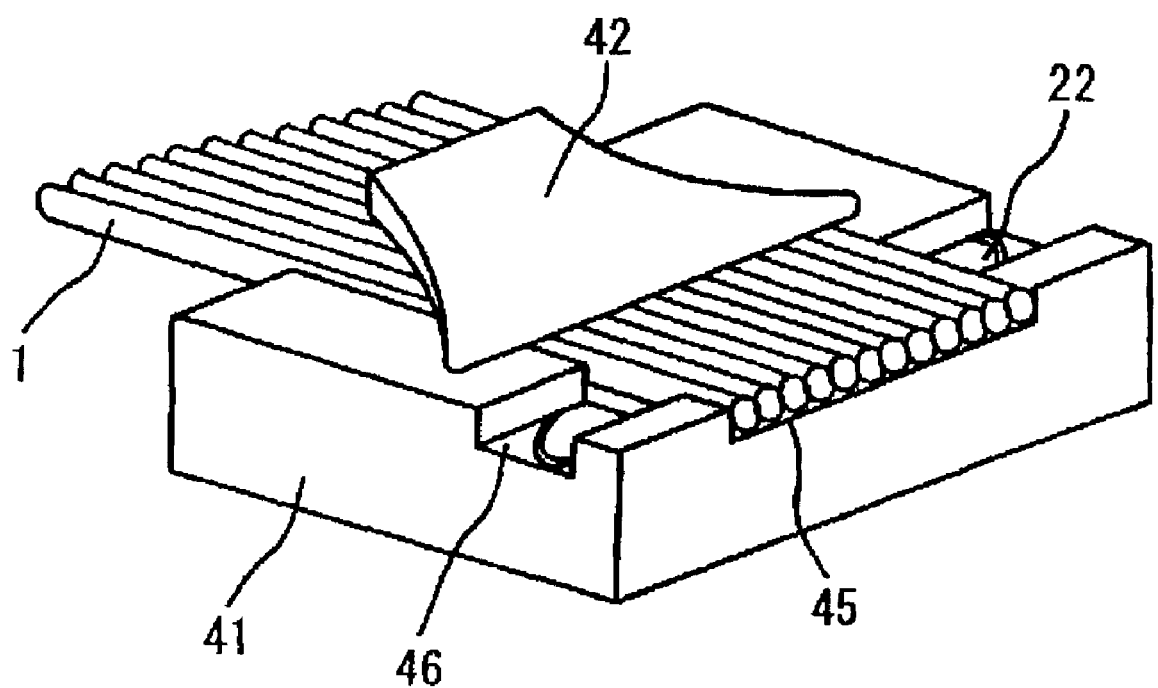
FIG. 13 is a schematic perspective view of the use of a bundle aligning table according to various embodiments.
Figure 14:
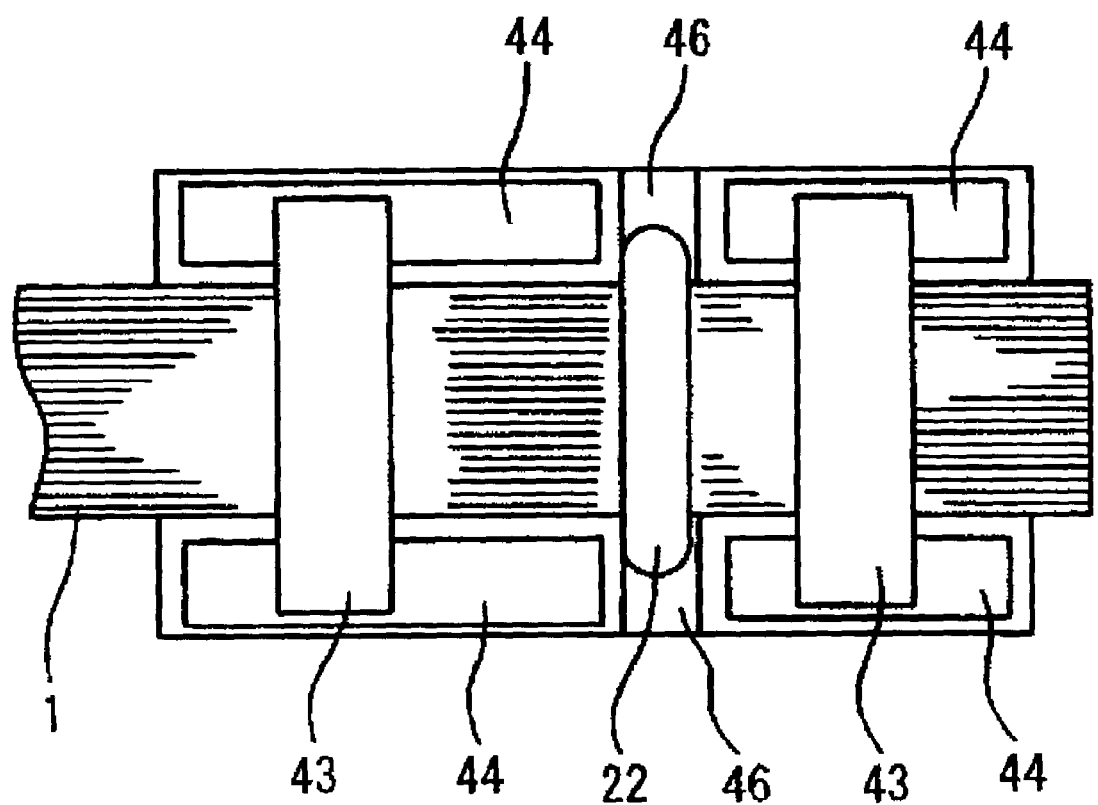
FIG. 14 is a top view of a bundle aligning table according to various embodiments.

FIGS. 13 and 14 illustrate a capillary bundle aligning mold 41 for preparing the ribbon-shaped member. The method of preparing the ribbon-shaped member will be disclosed with reference to FIGS. 13 and 14. In FIG. 13, the number of capillaries 1 shown is 12 to simplify the figure and more readily show the use of the capillary bundle aligning mold 41.

According to various embodiments, the capillary bundle aligning mold 41 has a slot 45, that can be formed from a fluorine-based resin, for example, sheet slot 46, and steel plates 44. When 96 capillaries 1 are to be aligned, for example, the slot 45 can have a width corresponding to the width of the 96 capillaries 1, for example, the width of the slot 45 can be about 14.5 mm and the depth of the slot 45 can be about 0.13 mm, and a length of the slot 45 can be about 300 mm. According to various embodiments, the surface material of the slot 45 can be made of a fluorine-based resin, for example. A sheet slot 46 can be arranged to be perpendicular to slot 45 and it can hold an aligned sheet in its recess. Two steel plates 44 can form a group, and they can be arranged outside each of the two sides of the slot 45.

According to various embodiments, when the ribbon-shaped member is prepared, the aligned sheet can be first arranged in the sheet slot 46. The aligned sheet can be a polyolefin sheet having a size of about 5 cm by about 22 cm, and can have a thickness of about 0.15 mm. The polyolefin sheet can be prepared by coating a polyolefin resin on PET (light plastic film).

According to various embodiments, the 96 capillaries 1 can be carried in the slot 45 with their end portions aligned with each other. The capillaries 1 can be lightly pressed with a flat plastic spatula 42. As the spatula 42 moves along a longitudinal direction of the slot 45, the capillaries 1 can be spread in the slot to form a ribbon shape. According to various embodiments, one end of the capillaries 1 can be fixed with a steel plate 44 by way of a hammer and a magnet. In this way, the operation of moving the spatula 42 in the direction of the slot 45 can be made easier. Because the surface material of the capillary bundle-aligning mold 41 is softer than the material of the capillaries 1, the capillaries 1 are not damaged during this operation. As a result, it is possible to reduce the danger of cutting or damaging the capillaries 1 in the later steps of operation, and during handling of the capillary array.

According to various embodiments, another aligned sheet can then be arranged over the capillaries 1, and the capillaries 1 can be held and hot-pressed, thereby forming a fixed member 22. As a result, it is possible to reliably fix the capillaries 1. The capillaries 1 can then be removed from the slot 46, and a ribbon-shaped member can be formed.

According to various embodiments, adhesive tape may be applied at one or two areas of the capillaries 1 when the capillaries 1 are arranged in a parallel relationship within the slot. According to various embodiments, after a ribbon-shaped member is formed from the capillaries 1 by way of the capillary bundle-aligning table, an adhesive can be coated on a portion of the capillaries 1, followed by curing.

FIGS. 5(*a*) and 5(*b*) are schematic diagrams illustrating the ribbon-shaped member made of a plurality of capillaries 1, for example, 96 capillaries.

According to various embodiments, the fixing member 22 can be prepared, for example, by heat-pressing two polyolefin sheets having a size of about 5 cm by about 22 cm, and having a thickness of about 0.15 mm. The capillaries 1 can be held between the two plastic films during the heat pressing. As a result, the 96 capillaries 1 can be arranged parallel to each other.

According to various embodiments, when the fixing member 22 is relatively hard and the capillaries 1 are bent, a force can be applied and concentrated at a contact boundary portion between the capillaries 1 and the fixing member 22. By providing the fixing member 22 with an appropriate softness, it is possible to avoid a concentration of stress on the capillaries 1, thereby preventing damage to the capillaries 1.

According to various embodiments, the fixing member 22 can be thin and can be in the shape of a sheet. This can allow the fixing member 22 to dissipate heat generated in the capillaries 1 during electrophoresis. The capillaries 1 can be adhered and connected to each other such that the temperature of the various capillaries 1 can be kept substantially uniform. As a result, the thermal characteristics of the capillaries 1 can be uniform and it is possible to avoid having the electrophoresis velocity depend on the capillaries 1.

According to various embodiments, when a high voltage is applied to the capillaries 1 during electrophoresis, any dust floating in the environment can be undesirably attracted to the capillaries 1. However, because there is no adhesive force found on the surface of the fixing member 22, no dust can be attached to the capillaries 1.

According to various embodiments, instead of heat pressing the plastic film, it is possible to use a plastic film with an adhesive material attached to fix the capillaries 1. Caution should be taken to avoid exposure of the adhesive material on the surface of the aligned sheet. According to various embodiments, the plastic film can be from about 0.05 mm to about 0.2 mm thick. The plastic film can be applied to the capillaries without the use of an adhesive material attached to it.

According to various embodiments, the capillaries 1 can be fixed by using a cured adhesive. When the cured adhesive is a rubber, or other elastic material, for example, the ribbon-shaped member can be handled while damage to the capillaries 1 can be substantially avoided.

According to various embodiments, fixing members 22 can be mounted on two sides of the detection cell 5, as shown in FIGS. 1(a), 1(b), 8(a), and 8(b). The fixing members 22 can be arranged relatively close to the detection cell 5. As a result, it is possible to facilitate the assembly of the capillaries 1 in the guide slot 46 of the detection cell 5 during the aligning and fixing step, the $6^{th}$ step. According to various embodiments, the fixing members 22 can be arranged at several sites along the capillaries 1 depending upon the structure of the capillary array and the method of preparing the detection cell 5.

Figure 15:
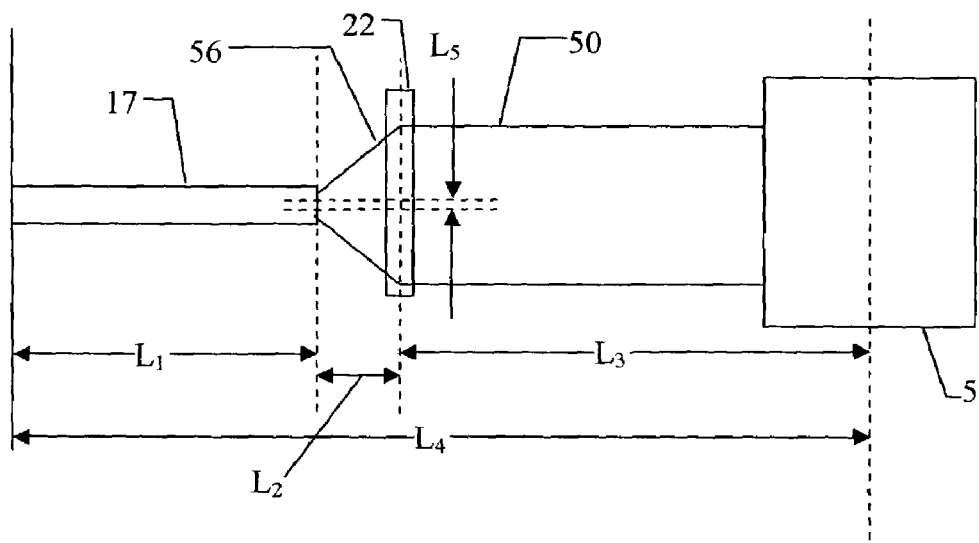
FIG. 15 is a schematic diagram of a top view of a capillary array according to various embodiments.

FIG. 15 schematically shows an exemplary capillary array having a fixing member 22 arranged between a capillary head 17 and a detection cell 5. FIG. 15 shows exemplary dimensions of the components, as well as distances between the components, of the capillary array. A length, $L_2$, of a diverging array of capillaries 56 can be defined by the distance between an end of the capillary head 17 and the fixing member 22. A length, $L_3$, of the ribbon-shaped member 50 can be defined by the distance between the fixing member 22 and the middle of the detection cell 5. A length of the capillary head 17 can be represented by $L_1$, while the length of the entire capillary array from an end of the capillary head 17 to the middle of the detection cell 5 can be represented by $L_4$.

Figure 6:
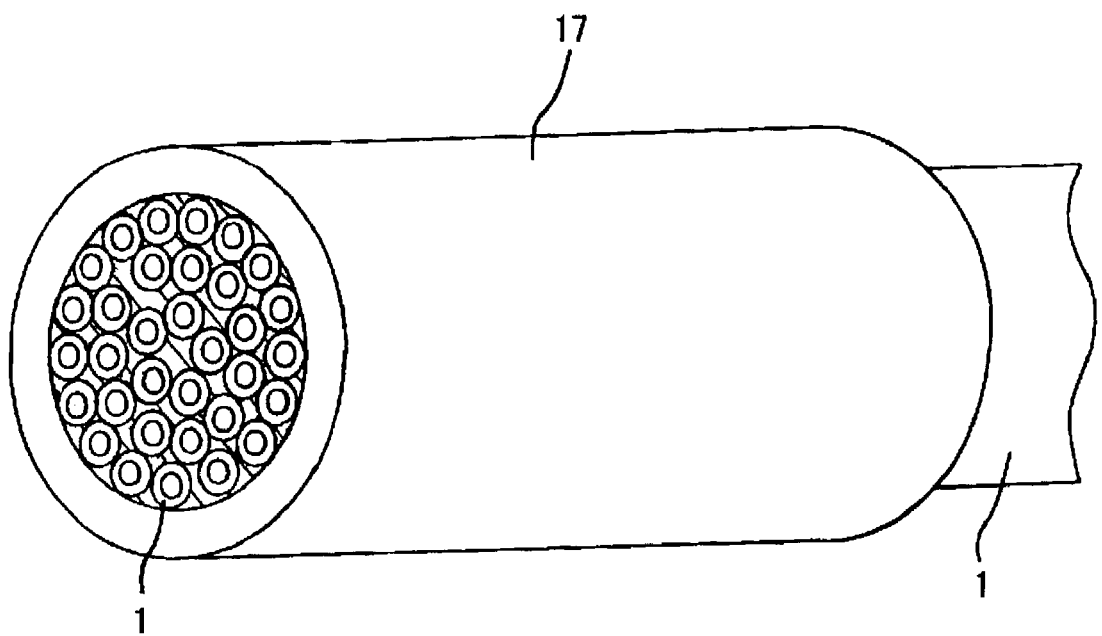
FIG. 6 is a schematic diagram of a load header according to various embodiments.

The capillary head mounting step ($4^{th}$ step). In this step, the opposite end portions of the capillaries 1 can be handled by inserting them into the cylindrical capillary head 17. FIG. 6 is a schematic diagram illustrating the cylindrical capillary head 17 prepared in this step. The cylindrical capillary head 17 can have a shape with a length of about 40 mm and a diameter of about one or more millimeters, for example. The cylindrical capillary head 17 can have a relatively small size and it can densely bundle the capillaries 1.

Figure 16:
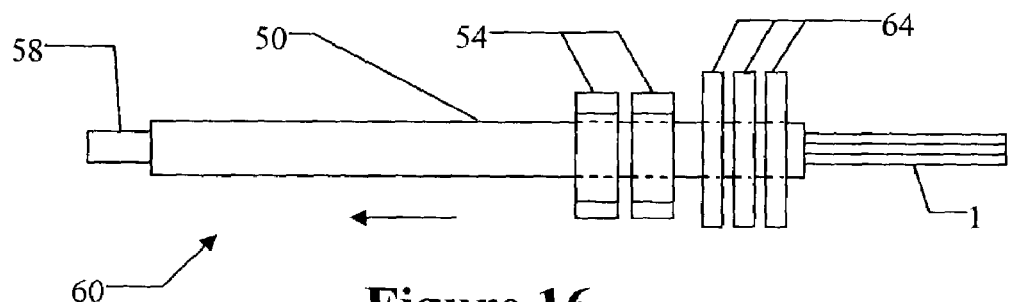
FIG. 16 is a side view of an array ferrule that can bundle the ends of the capillaries of a capillary array according to various embodiments.
Figure 17:
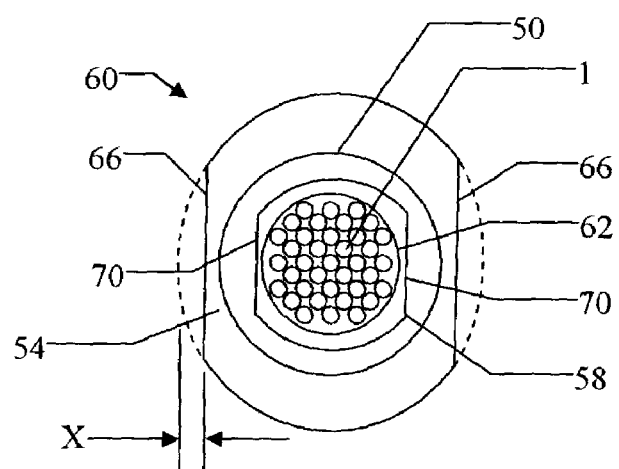
FIG. 17 is an end view of the array ferrule of FIG. 16 according to various embodiments.

FIGS. 16 and 17 show a side view and an end view, respectively, of an exemplary array ferrule 60. The array ferrule 60 can be used as a capillary head to bundle end portions of the capillaries 1, and allow an operator to readily handle and place the capillaries 1 in fluid communication with an electrophoresis system. For example, the array ferrule 60 can be used to place the capillaries 1 in fluid communication with the buffer container of an electrophoresis device. The array ferrule 60 can include a ferrule body 50 that can be a tubular member having a hollow inner portion 62 (represented in FIG. 15 by $L_5$). The opposite end portions of the capillaries 1 can be inserted into one end of the ferrule body 50, and pushed through the hollow inner portion 62, thereby bundling and supporting the capillaries within the ferrule body 50.

According to various embodiments, a reduced diameter portion 58 can be arranged at an opposite end of the ferrule body 50. The reduced diameter portion 58 can be provided with a cross-sectional shape that can allow the array ferrule 60 to be properly oriented when inserted, press-fitted for example, into a component of an electrophoresis device, such as a buffer container for example. The direction of insertion of the array ferrule 60 into a component of the electrophoresis device is shown by way of the arrow in FIG. 16.

According to various embodiments, an exemplary cross-sectional shape of the reduced diameter portion 58 is shown in FIG. 17, that illustrates an end view of the array ferrule 60 of FIG. 16. For example, the reduced diameter portion 58 can be provided with a 'D'-ring cross-sectional shape. The 'D'-ring shape of the reduced diameter portion 58 can be arranged to mate with a correspondingly shaped portion of the component into which the array ferrule 60 is inserted. As a result, the reduced diameter portion 58 can operate to provide an anti-rotation feature for the array ferrule 60, thereby preventing damage to the capillaries 1.

According to various embodiments, one or more removal rings 54 can be arranged along an outer surface of the ferrule body 50. The removal rings 54 can be arranged to allow the array ferrule 60 to be securely attached to the component by way of a friction-fit, for example. A further securing mechanism, such as a threaded nut device, that can be readily accessible by the operator, can be provided to additionally secure the friction fit of the removal rings 54 to the component by way of a jack screw effect, for example. According to various embodiments, the removal rings 54 can also provide heat exchange for the array ferrule 60 and the capillaries 1.

According to various embodiments, and as shown in FIG. 17, the removal rings 54 can be provided with flats 66. The flats 66 are arranged to be parallel to each other and can be formed by taking a cut out of two oppositely arranged portions of the outer surface of the removal rings 54. As shown in FIG. 17, the depth of the cuts can be represented by, X, and can be from about 0.02 inches to about 0.06 inches deep. According to various embodiments, the depth of the cuts, X, and can be about 0.04 inches. The flats 66 of the removal rings 54 can be oriented in the same direction, parallel for example, to the parallel arranged flats 70 of the 'D'-ring shaped reduced diameter portion 58. Such an orientation can be provided for the convenience of the operator and for achieving proper positioning of the array ferrule 60 relative to the component of the electrophoresis device into which the array ferrule 60 is inserted.

According to various embodiments and as shown in FIG. 16, one or more ribs 64 can be arranged along an outer surface of the ferrule body 50. The ribs 64 can facilitate the insertion and removal of the array ferrule 60 from the component of the electrophoresis device. The ability to securely hold the array ferrule 60 is desirable because it may be necessary to break a vacuum when disconnecting the capillaries 1 from the component of the electrophoresis device. The ribs 64 can allow an operator to readily grab and securely hold the array ferrule 60 during assembly and disassembly. The ribs 64 can also provide heat exchange for the cooling of the array ferrule 60 and the capillaries 1. According to various embodiments, the array ferrule 60 can be made of a material that is heat resistant, such as PEEK for example. As the result, the array ferrule 60 can be capable of resisting distortion while electrophoresis is performed.

The capillary coating removing step ($5^{th}$ step). In this step the ribbon-shaped member can be held in the slot of a coating-removing fixture, and only the portion of the capillaries 1 that are to have the polyimide coating removed is exposed to a thermostatically controlled ozone gas. In the conventional method, after burning and carbonizing the polyimide with, for example, a heater or infrared validation, it is removed with an external force, such as a brush. However, the capillaries may be damaged utilizing this conventional method. According to various embodiments, only the polyimide coating of a portion of the plurality of capillaries 1 is subject to ashing, and can then be removed. As a result, it is possible to remove the polyimide coating with high precision in a relatively short period of time, without applying an external force, such as a brushing force.

Figure 4A:
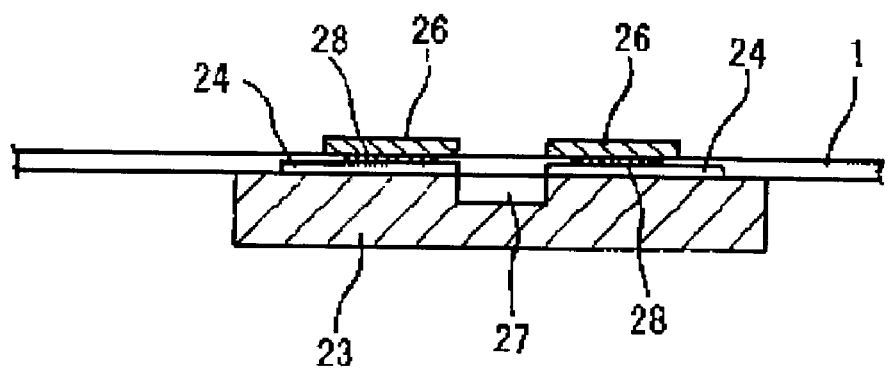
FIG. 4(a) is a side view of a detection cell according to various embodiments.
Figure 4B:
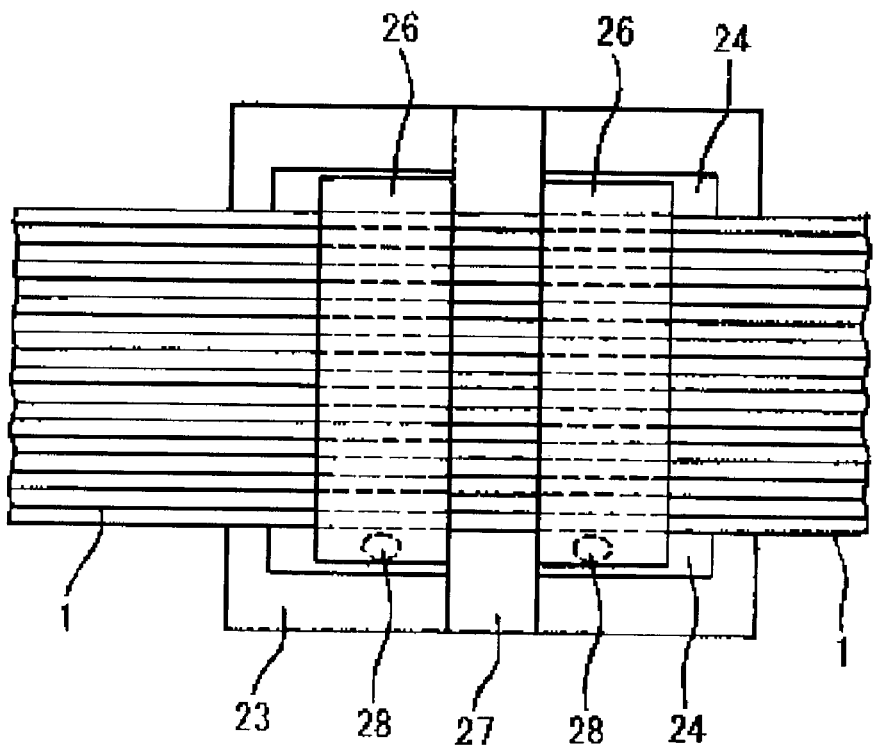
FIG. 4(b) is a top view of the detection cell of FIG. 4(a) according to various embodiments.
Figure 4C:
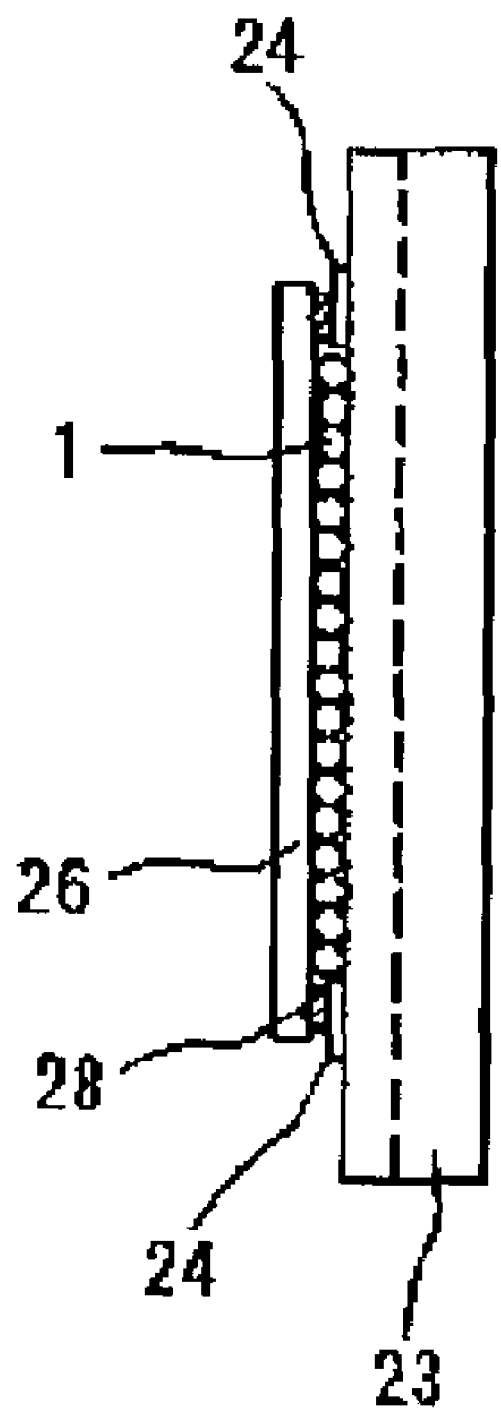
FIG. 4(c) is an end view of the detection cell of FIG. 4(b) according to various embodiments.

Step of aligning and fixing on reference base ($6^{th}$ step). FIGS. 4(a)-4(c) illustrate in detail the structure of the detection cell 5 that can be prepared in this step. FIG. 4(a) is a side view as seen from a direction perpendicular to the capillaries 1. FIG. 4(b) is a top view as shown from above the reference base 23. FIG. 4(c) is a side cross-sectional end view as seen from a direction looking into the capillaries 1. For the detection cell 5, the 96 capillaries 1 can be aligned with a precision as high as a few micrometers on the reference base 23. The reference base 23 can be made of glass, for example. The capillaries 1 can be positioned with a high precision by way of two rows of guides 24 that can be bonded on the reference base 23. The capillaries 1 can be adhered and fixed on the reference base 23 by way of pressing plates 26 that can be made of an optical-quality polished glass or a silicon plate, for example. The pressing plates 26 can be fixed on the guides 24 with an adhesive 28 on the two sides of the slot 27, through which the laser beam can pass.

According to various embodiments, in this step, the ribbon-shaped member can be arranged between the guides 24, such that the coating-removed portion, arranged in the $5^{th}$ step, can be fit into the slot 27. By way of an adhesive 28, the pressing plates 26 can then be fixed on guides 24, and the ribbon-shaped member and the reference base 23 can be adhered and bonded to each other. If the capillaries 1 were to be arranged one-by-one on the reference base 23, more than about 1 hour could be need even for a skilled worker due to problems related to repulsion as a result of electrostatic effects. According to various embodiments, the operation can be finished in a few minutes, even by a novice. When the capillaries 1 are manipulated for a long time on a glass plate, there can be a high danger of damage to the capillaries 1, that can now be avoided.

As explained in the above example, the various embodiments allow an increase in the productivity of the capillary array. The capillary array can also be manufactured such that the influence of the capillaries on the electrophoretic velocity of the sample, is reduced or eliminated.

APPLICATION EXAMPLE 2

Figure 10:
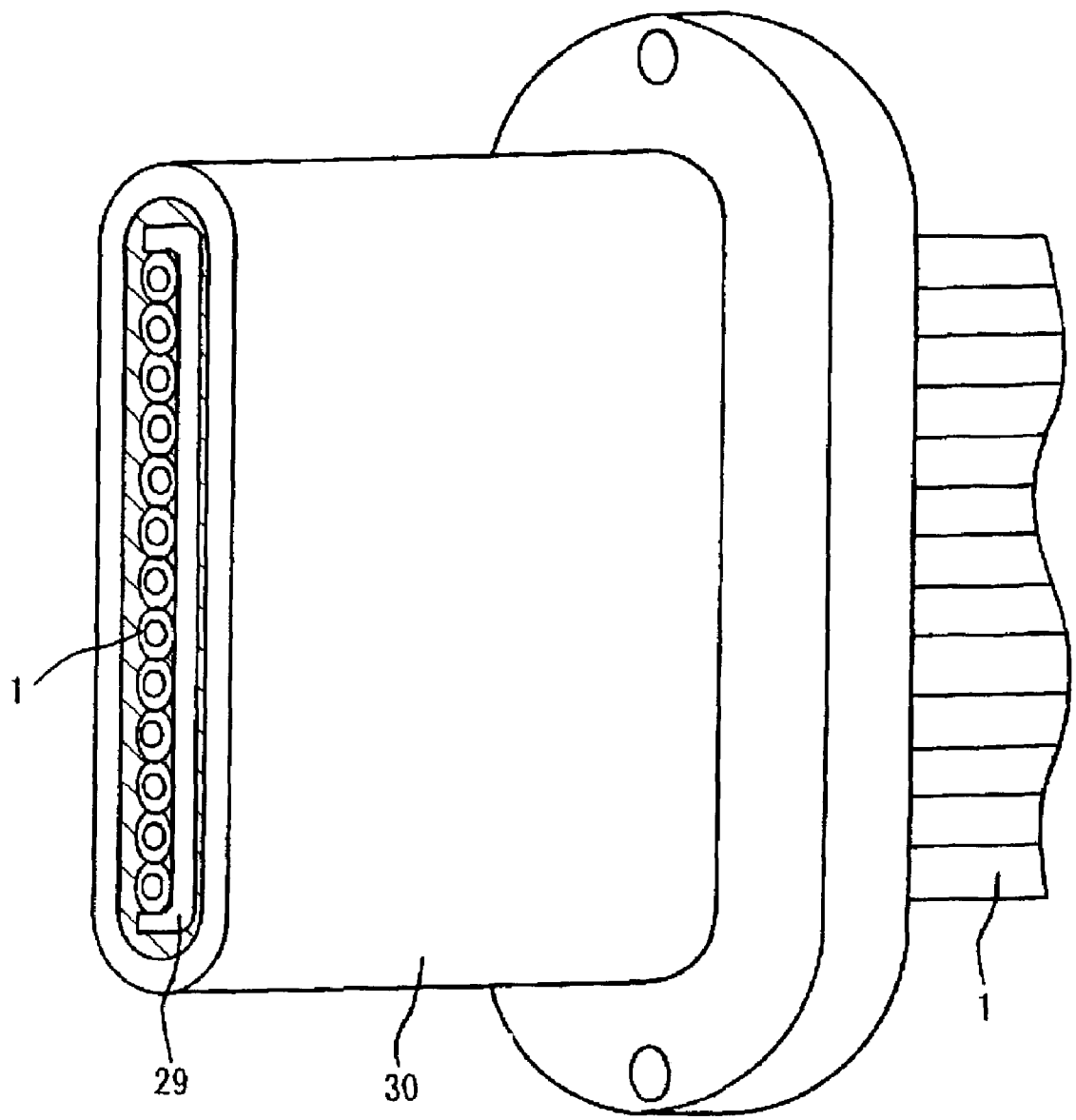
FIG. 10 is a schematic diagram of a plate-shaped capillary head according to various embodiments.

This example pertains to a type of capillary array having a capillary head that is in the shape of a plate. FIG. 10 is a schematic diagram illustrating a plate-shaped capillary head 30. In the following, only the features that are different from Application Example 1 will be referenced in FIG. 10.

According to various embodiments, to achieve a uniform electrophoresis velocity for a sample, such as a nucleic acid for example, and to achieve a constant separating power for the various capillaries, it is desirable to have a uniform temperature characteristics for each of the capillaries 1. In Application Example 1, the largest portion of the capillaries 1, that is, the portion between the detection cell 5 and the load header 17, can be loaded in a thermostatically controlled vessel. In the thermostatically controlled vessel, controlled air at a constant temperature can be circulated to ensure a uniform distribution of capillary temperature. However, in Application Example 1, in the structure of the optical system, the area in the vicinity of the detection cell 5 can be arranged outside the thermostatically controlled vessel, the end portions of the capillaries 1 can also be bundled by way of the capillary head 17. As a result, the spacing between the capillaries 1 can be irregular in the area between the capillary head 17 and the detection cell 5. As a result, the thermal characteristics between the detection cell 5 and the capillaries 1 can be different among the various capillaries 1.

According to various embodiments, during electrophoresis, a high voltage can be applied to the capillaries 1, and joule heat can be generated as a result of the electrophoresis current. The quantity of heat generated by each capillary can be about 50 to about 250 mW, and the total quantity of heat generated by 96 capillaries 1 can be about 5 to about 25 W. The capillary head 17 that bundles the capillaries 1 can generate about 2.5 to about 3 watts of heat. As a result, in the cylindrical capillary head 17 used in Application Example 1, the temperature increase during electrophoresis can be about 30° C. to about 50° C., resulting in problems occurring.

Figure 1A:
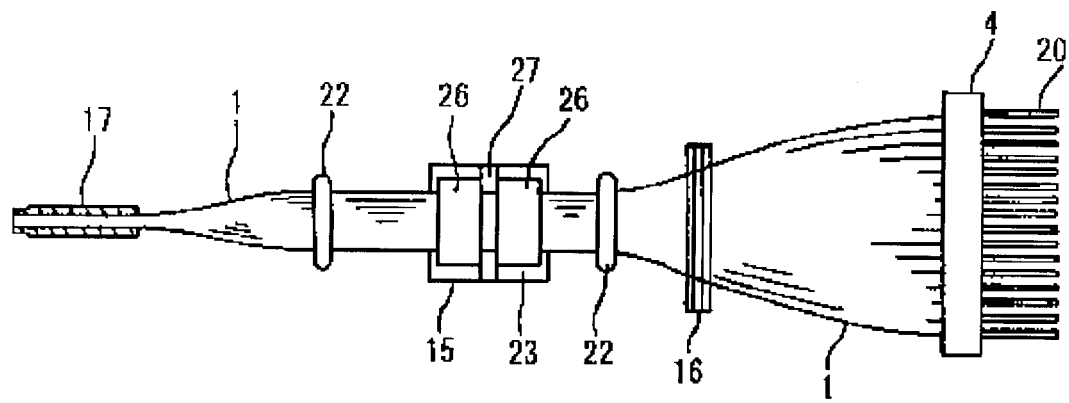
FIG. 1(a) is a schematic drawing of a top view of an intermediate portion of a capillary array, according to various embodiments.
Figure 1B:
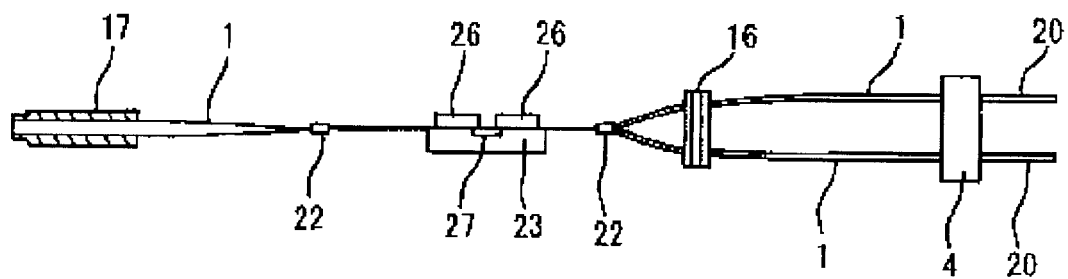
FIG. 1(b) is a schematic drawing of a side view of the intermediate portion of the capillary array of FIG. 1(a), according to various embodiments.

According to various embodiments, in this example and in consideration of these problems, the capillary accommodating portion of the capillary head 17 can have an elliptical shape with a relatively small width, as shown in FIG. 1(a). The capillaries 1 can be arranged in a row as they are bonded on a capillary fixing plate 29, and they can be coupled to the plate-shaped capillary head 30. As a result, it is possible to provide uniform capillary heat dissipation conditions between the capillary head and the detection cell. The influence of the capillaries 1 on the electrophoretic velocity of the sample can also be reduced.

APPLICATION EXAMPLE 3

Figure 11:
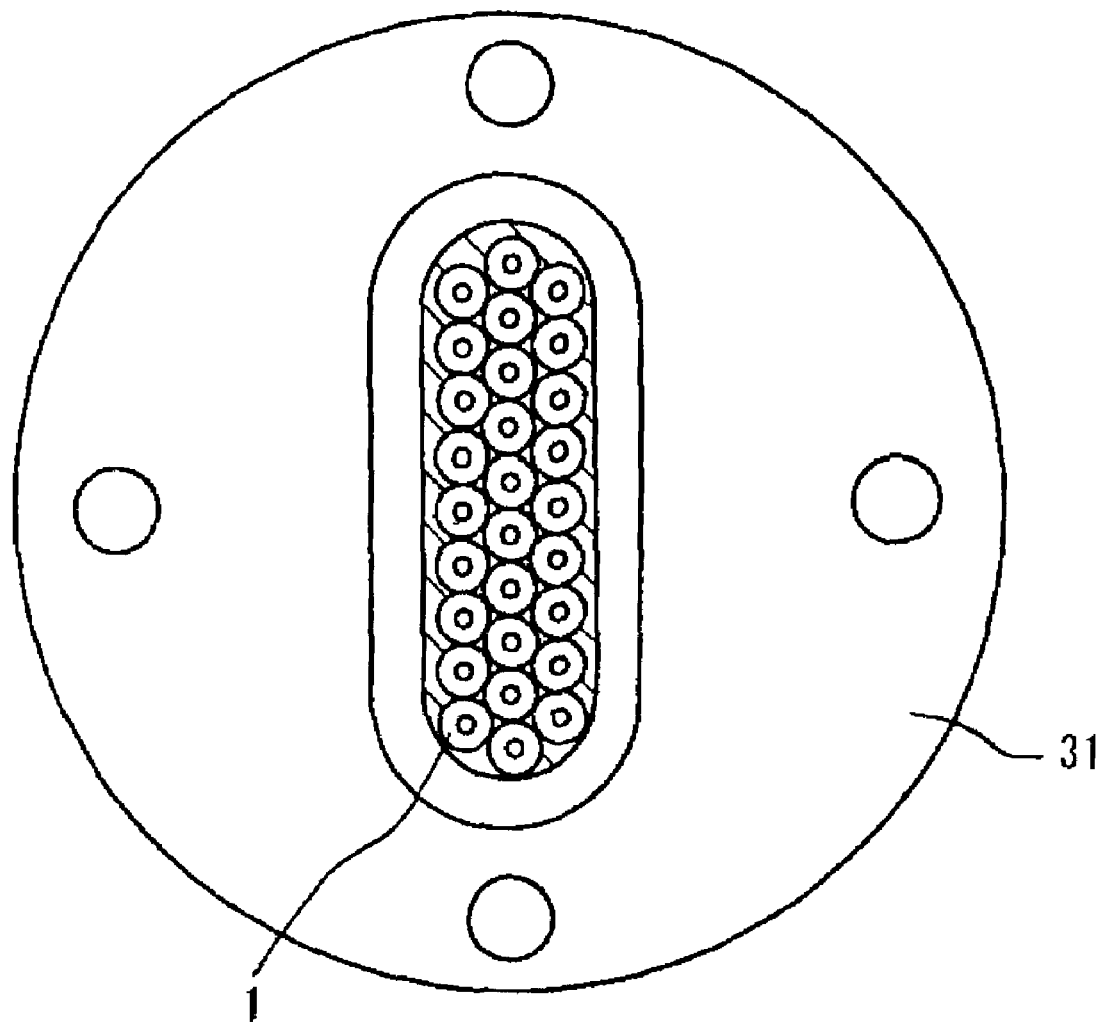
FIG. 11 is a schematic diagram of a plate-shaped capillary head according to various embodiments.

This example pertains to a type of capillary array having a laminated plate-shaped capillary head prepared by arranging a plurality of capillaries in 3-layer plate shape. FIG. 11 is a schematic diagram illustrating a laminated plate-shaped capillary head 31. In the following, the differences between Application Examples 1 and 2 will be discussed by reference to FIG. 11.

In this example, the laminated plate-shaped capillary head 31 can have a plurality of capillaries 1, 96 capillaries for example, that can be arranged in a 3-layer plate-shaped configuration. The three collection bodies, each prepared by arranging a third of the total number of capillaries side-by-side in a parallel relationship, can be laminated. Among the three layers, the capillaries 1 in the intermediate layer can be sandwiched between outer-layer capillaries 1 so that they can achieve good heat dissipation characteristics, and a thermal gradient can be prevented from forming in the capillaries 1 of the intermediate layer. As a result, compared with a round-shaped capillary head, a larger heat dissipation area can be achieved.

According to various embodiments, the need to use a fixing plate 29 to arrange the capillaries 1 side by side in a planar shape can be eliminated. The need to bond the plurality of capillaries 1 to a fixing plate can also be eliminated. As a result, compared with the planar-shape capillary head, this configuration can be more readily assembled. The need to prepare an expensive plate-shaped head, can also be eliminated allowing the system to be prepared at a lower cost.

APPLICATION EXAMPLE 4

Figure 7:
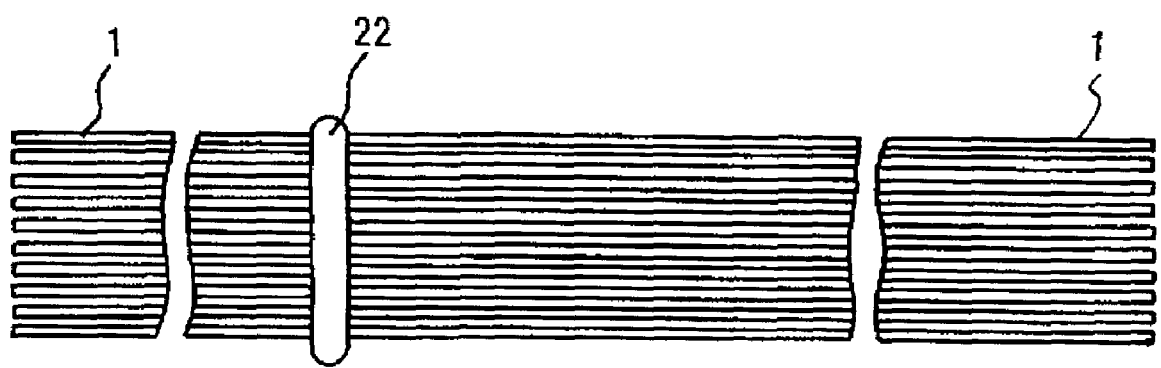
FIG. 7 is a schematic diagram of a top view of a ribbon-shaped member according to various embodiments.

This example pertains to a type of capillary array having a prescribed spacing arranged between capillaries and having a ribbon-shaped capillary body. FIG. 7 is a schematic diagram illustrating the ribbon-shaped capillary body having such a spacing. In the following, the disclosure will be made to the features that are different from Application Example 1, by referring to FIG. 7.

According to various embodiments, the spacing of the ribbon-shaped capillary body is prepared by thinning out every other capillary of the ribbon-shaped capillary body. Bumps and dips can be formed in the slot 45 of the aligning mold 41 as was disclosed in Example 1 Each of the capillaries 1 can then be fit into the dips. According to various embodiments, the aligning table, or a surface of the aligning table, can be made of a fluorine-based resin.

According to various embodiments, the capillary array prepared using the ribbon-shaped capillary body can be provided with a predetermined spacing between the plurality of capillaries. As a result, the heat-generating density can be lowered, and heat dissipation can be performed along the entire circumference of the capillaries 1. As a result, each capillary 1 is not affected by heat from each of its neighboring capillaries 1. It is then possible to achieve a uniform heat dissipation properties for all of the capillaries 1. It is also possible to alleviate the influence of wavelengths of light from adjacent capillaries, also referred to as cross-talk phenomenon. In this example, the spacing between capillaries can equal the thickness of a capillary. However, the spacing is not limited to such a dimension to achieve the aforementioned benefits.

APPLICATION EXAMPLE 5

Figure 9:
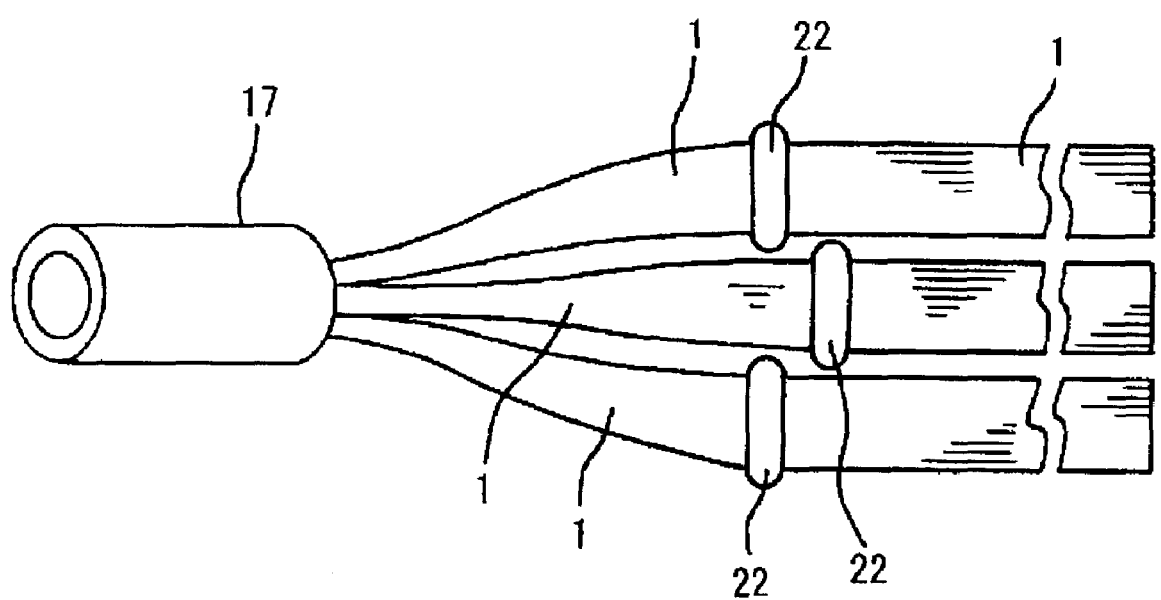
FIG. 9 is a schematic diagram of a top view of an intermediate portion of a divided-type capillary array according to various embodiments.

This example pertains to a type of capillary array prepared by dividing a plurality of capillaries 1 into three groups, and forming each group into a ribbon-shaped member. FIG. 9 is a schematic diagram of the three ribbon-shaped capillary members. In the following, the features that are different from those of Example 1 will be referred to in FIG. 9.

In this example, three groups of ribbon-shaped members, each of which can be composed of 32 capillaries, for example, can be used to form the capillary array. When the capillary array is prepared, three groups of ribbon-shaped members can be formed. The three ribbon-shaped members can then be sequentially divided when the capillaries 1 are arranged on a reference base. As a result, the detection cell can be formed relatively easily. When the capillary array is manufactured with multiple ribbon-shaped members, as the number of capillaries is increased from 48 to 96, for example, the benefits can be increased. The number of capillaries for each group can be determined depending upon the configuration of the sample containers arranged on the sample tray. According to various embodiments, it is desirable when the number of capillaries in each group is a multiple of 4. According to various embodiments, it is possible to manufacture multiple types of ribbon-shaped members by changing the number of capillaries arranged in each ribbon-shaped member. For example, when 16-capillary ribbon-shaped members are prepared, one can form capillary arrays with a total number of 16, 48, or 96 capillaries, for example.

APPLICATION EXAMPLE 6

Figure 12A:
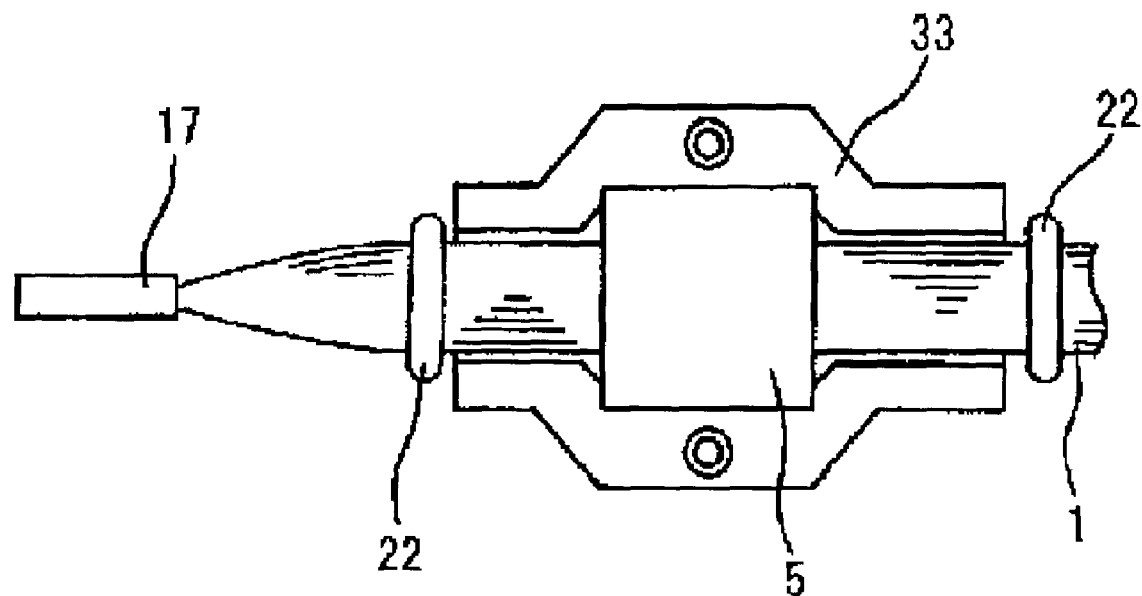
FIG. 12(a) is a detailed top view of a detection cell during assembly according to various embodiments.
Figure 12B:
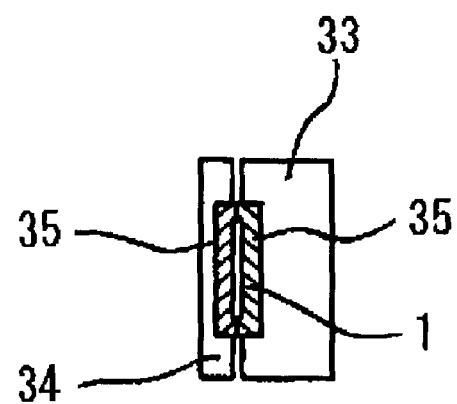
FIG. 12(b) is a diagram showing a side view of a detection cell according to various embodiments.

This example pertains to the location of the bundle alignment near the detection cell. The detection cell can be sandwiched with electrical heating sheets when the detection cell is assembled on the main body of the device. FIGS. 12(*a*) and 12(*b*) are schematic diagrams of the vicinity of the detection cell during assembly. In the following, this example will be explained with reference to FIGS. 12(*a*) and 12(*b*).

In Example 1, due to the structure of the optical system, the area in and around the detection cell can be assembled outside the thermostatically controlled vessel. The capillary end portions of the capillaries can be bundled by way of a capillary head. As a result, the portion of the capillaries between the capillary head and the detection cell are not held. Thus, the spacing between the capillaries can be irregular. As a result, the thermal characteristics of the portion of the capillaries between the detection cell and the capillary head can be different for different capillaries, and the electrophoresis velocities of the sample can be different for different capillaries.

In this example, the fixing member 22 can be arranged such that the capillaries 1 near the detection cell 5 can be arranged substantially parallel. During assembly, the parallel capillaries 1 can be sandwiched and held between a mounting holder 33 of the main body of the device and a holder cover 34. The parallel capillaries 1 can be partially bonded with the mounting holder 33 and the holder cover 34, and they can be held with a thermal conductive sheet 35. If there were to be no such fixing member, during assembly the plurality of capillaries could be overlapped with each other as they are sandwiched between the mounting holder 33 and the holder cover 34. In such a situation, the capillaries 1 could be damaged. However, in this example, this problem can be avoided. As a result, it can be possible to assemble the capillary array in the main body of the device in a safe and reliable manner.

According to various embodiments, the parallel capillaries 1 can be held by two foam pads at 35, when held between the mounting holder 33 and the holder cover 34. The foam pads can transfer heat to the detection cell 5, that can be made of aluminum, for example, to dissipate heat more evenly. As a result, the separation medium can be prevented from out-gassing or boiling.

According to various embodiments, the plurality of capillaries can be in contact with the thermal conductive sheet 35, and the thermal characteristics of the capillaries can become uniform.

APPLICATION EXAMPLE 7

Figure 8A:
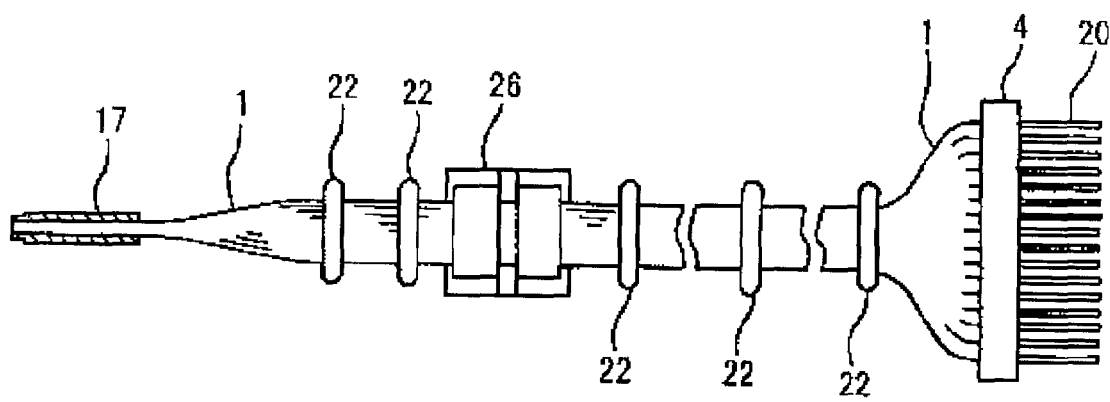
FIG. 8(a) is a schematic diagram of a top view of an intermediate portion of a capillary array according to various embodiments.
Figure 8B:
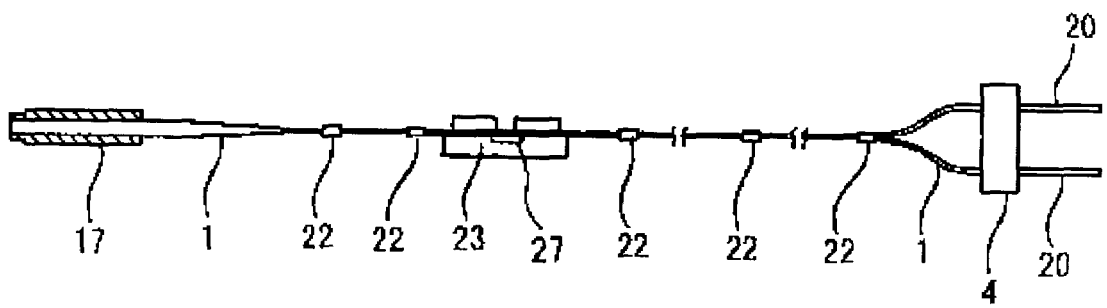
FIG. 8(b) is a schematic diagram of a side view of the intermediate portion of the capillary array of FIG. 8(a) according to various embodiments.

In this example, the capillaries 1 between the load header 4 and detection cell 5 can be arranged substantially parallel to each other by arranging fixing members 22 between them, without using a separator 16. FIGS. 8(a) and 8(b) are schematic diagrams illustrating an intermediate portion of the capillaries 1 that can be arranged substantially parallel to each other by way of fixing members 22 between the load header 4 and the detection cell 5. In the following this example will be explained with reference to FIGS. 8(a) and 8(b).

According to various embodiments, most of the capillaries of the capillary array can be arranged in a parallel relationship by way of fixing members 22. The capillaries in the portion immediately after the load header 4 and immediately before the capillary head 17 can be arranged parallel to each other, and can have substantially the same spacing between them. As a result heat dissipation characteristics of the various capillaries can be substantially uniform. By way of the fixing members 22, the spacing can be kept nearly constant for the various capillaries. Even when there is a change in the three-dimensional shape of the capillaries due to airflow in the thermostatically controlled vessel, the heat dissipation characteristics of the various capillaries can still be substantially uniform. In addition, it can be easy to manufacture the capillary array because there is no need to use a separator According to various embodiments, the productivity of the capillary array can be improved and the influence of the capillaries on the electrophoresis velocity can be reduced.

Those skilled in the art can appreciate from the foregoing description that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

What is claimed is:

1. A method of manufacturing a capillary array comprising:
   providing a plurality of capillaries each being capable of being filled with a separation medium, each capillary including an inlet end portion that is capable of feeding a sample into the capillary and a light-illuminable portion that is capable of allowing the sample to be illuminated with light;
   arranging the plurality of capillaries substantially parallel to each other along a substantially flat plane;
   fixing a portion of the plurality of capillaries that are arranged substantially parallel to each other by hot-pressing a fixing member comprising a plastic film onto the plurality of capillaries;
   preparing a ribbon-shaped member formed by the plurality of substantially parallel capillaries; and
   arranging a detection cell comprising a side slot, at a location on the ribbon-shaped member separate from the fixing member, such that the detection cell is arranged substantially parallel to the light-illuminable portions of the plurality of capillaries and the side slot is aligned perpendicular to the light illuminable portion and parallel to the flat plane;
   wherein the fixing member is spaced apart from the detection cell, and the capillaries are arranged equally spaced and parallel from the fixing member to the detection cell, and inside the detection cell.

2. The method of claim 1, wherein arranging the plurality of capillaries substantially parallel to each other along a substantially flat plane includes pressing the plurality of capillaries into a substantially planar slot formed in a capillary bundle-aligning mold, the capillary bundle-aligning mold being formed from a material that is softer than a material forming the plurality of capillaries.

3. The method of claim 1, wherein the fixing member is in the shape of a sheet.

4. The method of claim 1, wherein fixing a portion of the plurality of capillaries with a fixing member further includes curing a fluidic resin onto the plurality of capillaries.

5. The method of claim 1, wherein arranging the plurality of capillaries substantially parallel to each other includes providing a substantially equal spacing between each of the capillaries.

6. The method of claim 1, further comprising bundling together opposite end portions of the plurality of capillaries with a capillary head, the capillary head including an array ferrule including a rotation prevention mechanism.

7. The method of claim 1, further comprising bundling together opposite end portions of the plurality of capillaries with a capillary head, the capillary head including an array ferrule including a heat exchange structure.

8. A capillary array comprising:
   a plurality of capillaries each capable of being filled with a separating medium for separating a sample, each capillary including an inlet end portion for feeding a sample, an opposite end portion arranged opposite to the inlet end portion, and a light-illuminable portion capable of being illuminated with light, the light-illuminable portions being arranged in a flat plane;
   a load header arranged to support the inlet end portions of the plurality of capillaries at a predetermined position;
   a capillary head arranged to support the opposite end portions of the plurality of capillaries;
   a detection cell comprising a side slot, the detection cell arranged substantially parallel to the light-illuminable portions of the plurality of capillaries and the side slot being aligned perpendicular to the light illuminable portions and parallel to the flat plane; and
   a fixing member comprising a hot-pressed plastic film and arranged to support a portion of the plurality of capillaries substantially parallel to one another;
   wherein the fixing member is spaced apart and separate from the detection cell, and the capillaries are arranged equally spaced and parallel from the fixing member to the detection cell, and inside the detection cell.

9. The capillary array of claim 8, wherein the fixing member is made of a material that is softer than the material of the plurality of capillaries.

10. The capillary array of claim 8, wherein a surface of the fixing member has non-adhesive properties during electrophoresis.

11. The capillary array of claim 8, wherein the fixing member is in the shape of a sheet.

12. The capillary array of claim 8, wherein the fixing member is made of a cured fluidic resin.

13. The capillary array of claim 8, wherein the portion of the plurality of capillaries supported by the fixing member are adhered to each other.

14. The capillary array of claim 8, wherein the fixing member is arranged on a first side of the detection cell and a second fixing member is arranged on a side of the detection cell opposite the first side.

15. The capillary array of claim 8, wherein the capillary head is an array ferrule including a rotation prevention mechanism.

16. The capillary array of claim 15, wherein the rotation prevention mechanism includes a shaped member arranged on an end of the array ferrule that is capable of mating with a correspondingly shaped portion of a capillary electrophoresis device.

17. The capillary array of claim 16, wherein the shaped member has a D-ring cross-sectional shape.

18. The capillary array of claim 8, wherein the capillary head is an array ferrule including a heat exchange structure.

19. An electrophoresis device comprising:
- a plurality of capillaries each capable of being filled with a separating medium for separating a sample, each capillary including an inlet end portion for feeding a sample, an opposite end portion arranged opposite to the inlet end portion, and a light-illuminable portion capable of being illuminated with light, the light-illuminable portions being arranged in a flat plane;
- a detection cell comprising a side slot, the detection cell arranged substantially parallel to the light-illuminable portions and the side slot being aligned perpendicular to the light illuminable portions and parallel to the flat plane;
- a fixing member comprising a hot-pressed plastic film and ranged to support a portion of the plurality of capillaries substantially parallel to one another
- a sample tray capable of holding a plurality of samples;
- a voltage mechanism that is capable of applying a voltage between at least the inlet end portions of the capillaries and the light-illuminable portions of the capillaries;
- a pumping optical mechanism capable of directing light onto the light-illuminable portions of the capillaries; and
- a detecting optical mechanism that is capable of detecting light emitted from the light-illuminable portions of the capillaries;
- wherein the fixing member is spaced apart and separate from the detection cell, and the capillaries are arranged equally spaced and parallel from the fixing member to detection cell, and inside the detection cell.

20. The electrophoresis device of claim 19, wherein the fixing member is made of a material that is softer than the plurality of capillaries.

21. The electrophoresis device of claim 19, wherein a surface of the fixing member has non-adhesive properties during electrophoresis.

22. The electrophoresis device of claim 19, wherein the fixing member is in the shape of a sheet.

23. The electrophoresis device of claim 19, wherein the fixing member is made of a cured fluidic resin.

24. The electrophoresis device of claim 19, wherein the portion of the plurality of capillaries supported by the fixing member are adhered to each other.

25. The electrophoresis device of claim 19, further comprising an array ferrule arranged to bundle the opposite end portions of the plurality of capillaries.

26. The electrophoresis device of claim 25, wherein the away ferrule includes a rotation prevention mechanism.

27. The electrophoresis device of claim 25, wherein the array ferrule includes a heat exchange structure.

* * * * *